United States Patent
Agarwal et al.

(10) Patent No.: US 9,604,906 B2
(45) Date of Patent: Mar. 28, 2017

(54) PROCESS FOR THE PREPARATION OF 3-ARYLOXY-3-PHENYLPROPYLAMINE AND SALT THEREOF

(71) Applicant: ZCL CHEMICALS LIMITED, Mumbai (IN)

(72) Inventors: Nand Lal Agarwal, Bharuch (IN); Pranav Popatlal Mistri, Bharuch (IN); Trushar Dahyabhai Patel, Bharuch (IN); Pankaj Jayantilal Makasana, Bharuch (IN)

(73) Assignee: ZCL CHEMICALS LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/773,397

(22) PCT Filed: Jun. 17, 2014

(86) PCT No.: PCT/IN2014/000404
§ 371 (c)(1),
(2) Date: Sep. 8, 2015

(87) PCT Pub. No.: WO2015/001565
PCT Pub. Date: Jan. 8, 2015

(65) Prior Publication Data
US 2016/0107983 A1    Apr. 21, 2016

(30) Foreign Application Priority Data
Jul. 2, 2013 (IN) .......... 2234/MUM/2013

(51) Int. Cl.
C07C 213/10 (2006.01)
C07C 213/06 (2006.01)
C07C 213/08 (2006.01)

(52) U.S. Cl.
CPC .......... *C07C 213/10* (2013.01); *C07C 213/06* (2013.01); *C07C 213/08* (2013.01); *C07B 2200/07* (2013.01)

(58) Field of Classification Search
None
See application file for complete search history.

(56) References Cited

U.S. PATENT DOCUMENTS

| | | | | |
|---|---|---|---|---|
| 4,018,771 A | * | 4/1977 | Gupton, III | C07D 239/36 544/319 |
| 2006/0009532 A1 | * | 1/2006 | Castelli | C07C 213/06 514/646 |

FOREIGN PATENT DOCUMENTS

| | | | | |
|---|---|---|---|---|
| ID | WO2009141833 | * | 11/2009 | ........... C07C 213/06 |
| WO | 2006/009884 A1 | | 1/2006 | |
| WO | WO2006009884 | * | 1/2006 | ........... C07C 213/00 |
| WO | 2006/037055 A1 | | 4/2006 | |
| WO | 2008/062473 A1 | | 5/2008 | |
| WO | 2009/141833 A2 | | 11/2009 | |

\* cited by examiner

*Primary Examiner* — Clinton Brooks
(74) *Attorney, Agent, or Firm* — Prakash Nama; Global IP Services, PLLC

(57) ABSTRACT

The present invention relates to an industrially feasible and economically viable process for the preparation of 3-aryloxy-3-phenylpropylamine and salt of formula I thereof.

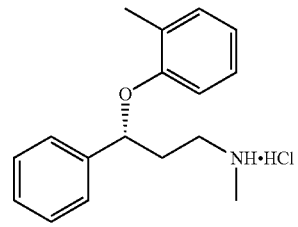

Formula I

10 Claims, No Drawings

PROCESS FOR THE PREPARATION OF 3-ARYLOXY-3-PHENYLPROPYLAMINE AND SALT THEREOF

FIELD OF THE INVENTION

The present invention relates to an improved and industrially applicable process for the preparation of 3-aryloxy-3-phenylpropylamine and salt of formula I thereof, Formula I

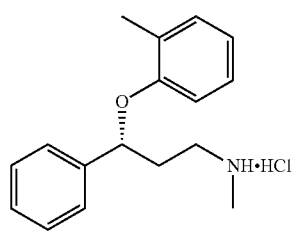

BACKGROUND OF THE INVENTION

Atomoxetine is the (R)-(−)-enantiomer of Tomoxetine, is an 3-aryloxy-3-phenyl propylamine structurally represented by the compound of Formula-I, a selective norepinephrine reuptake inhibitor, marketed as hydrochloride salt under the name of STRATTERA® used for the treatment of Attention Deficit Hyperactivity Disorder (ADHD). It is about 2 times effective than racemic mixture, about 9 times effective than (+)-enantiomer and exhibits less anticholinergic side effects as disclosed in U.S. Pat. No. 4,018,895, EP 0 052 492 and EP 0 721 777.

U.S. Pat. No. 4,314,081 discloses a process for preparation of N-methyl-3-(o-tolyloxy)-3-phenylpropylamine hydrochloride along with other compounds. One of the disclosed process for preparation of N-methyl 3-(o-tolyloxy)-3-phenylpropylamine involves the reaction of N,N-dimethyl-3-phenyl-3-chloro propyl amine hydrochloride with sodium salt of the corresponding phenol in methanol followed by demethylation using cyanogen bromide in benzene. The demethylated compound resolved by unspecified procedure and subsequently converted to hydrochloride salt by using gaseous hydrogen chloride.

The reaction of N,N-dimethyl-3-phenyl-3-halopropyl amine hydrochloride with sodium salt of the corresponding phenol in methanol is a time consuming process, requires about five days for completion of reaction. The whole process involves several unit operations. Further involves use of commercial grade o-cresol at plant level which contains phenol, p-cresol and 2,6-xylenol as impurities. These impurities can be carried forward to the final stage; hence exhaustive purification is required to remove the impurities. Use of benzene, thionyl chloride, cyanogen bromide and dry HCl gas are also major drawbacks of the process and makes it unattractive from the safety point of view, environmentally, economically and industrially. Moreover, the patent is silent about purity and yield of the atomoxetine or salts thereof.

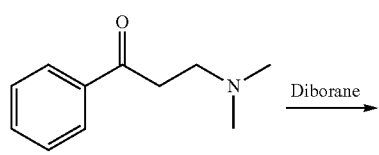

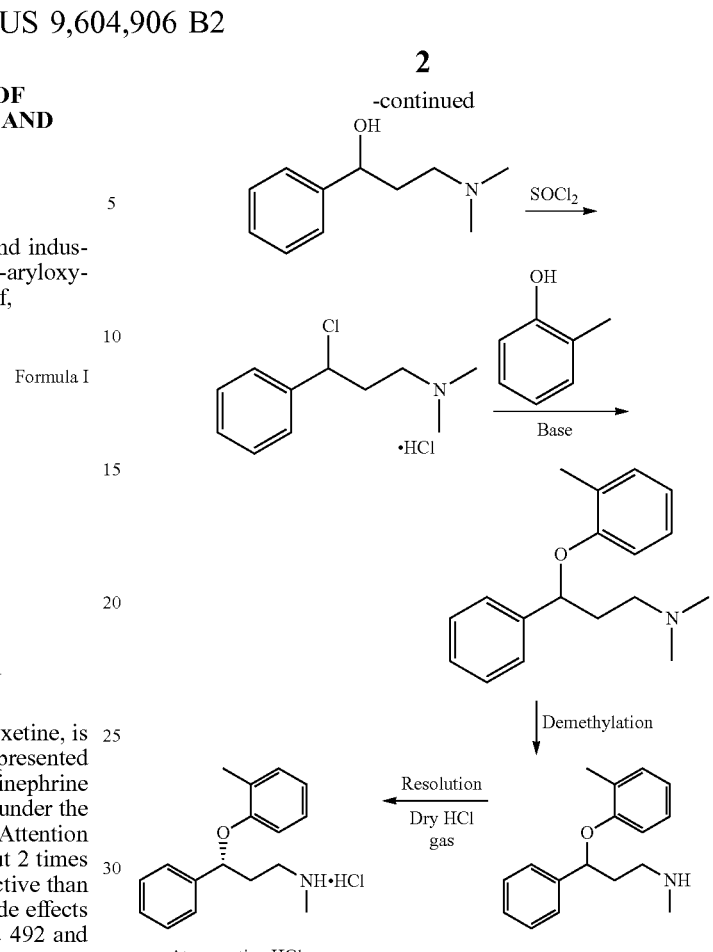

Atomoxetine HCl

The alternate process disclosed in same U.S. Pat. No. 4,314,081 involves the bromination of 3-phenylchloropropyl amine with N-Bromosuccinimide (NBS) in presence of benzoyl peroxide in carbon tetrachloride. The bromination reaction is exothermic reaction. The brominated compound is condensed with dry sodium salt of o-cresol followed by amination with methyl amine at temperature as high as 140° C. for 12 hours. The aminated compound is resolved by unspecified procedure to give atomoxetine.

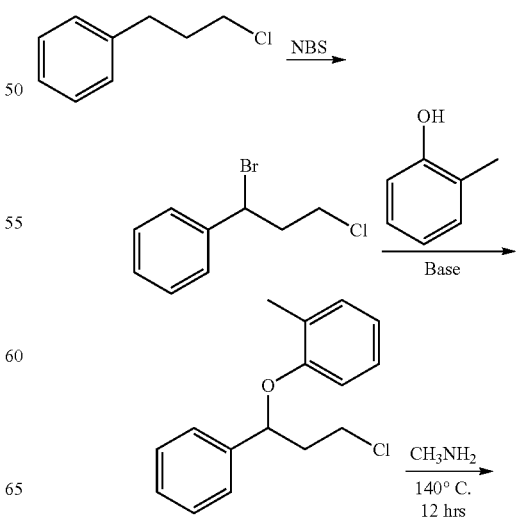

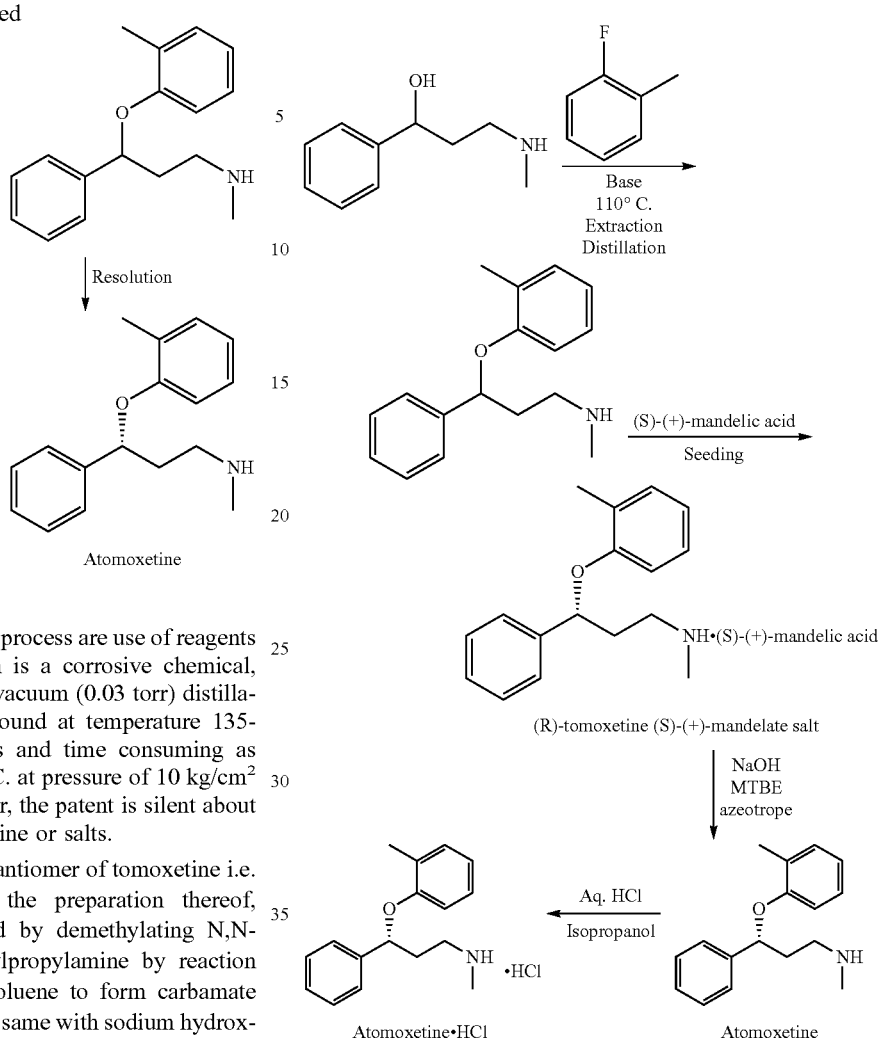

Atomoxetine

The main disadvantages of the process are use of reagents like N-bromosuccinimide which is a corrosive chemical, unfavorable condition like high vacuum (0.03 torr) distillation of condensed chloro compound at temperature 135-145° C. The process is tedious and time consuming as amination is conducted at 140° C. at pressure of 10 kg/cm$^2$ for 12 hours in autoclave. Further, the patent is silent about purity and yield of the atomoxetine or salts.

EP 0 052 492 discloses (−)-enantiomer of tomoxetine i.e. atomoxetine and process for the preparation thereof, wherein tomoxetine is prepared by demethylating N,N-dimethyl 3-(o-tolyloxy)-3-phenylpropylamine by reaction with phenyl chloroformate in toluene to form carbamate intermediate and hydrolyzing the same with sodium hydroxide in the presence of propylene glycol to form tomoxetine. Tomoxetine is then treated with (S)-(+)-mandelic acid followed by basification and extraction in diethyl ether. The resulting atomoxetine is treated with hydrogen chloride gas to afford atomoxetine hydrochloride. Atomoxetine hydrochloride is then recrystallized from ethyl acetate, dichloromethane and diethyl ether. The patent describes the use of propylene glycol which is a costly reagent, hence not recommended on industrial scale. Further the demethylation reaction involves very long and tedious procedure for reaction as well as workup, and then demethylated compound is crystallized by triturating with hexane and recrystallized by diethyl ether and methylene chloride.

U.S. Pat. No. 6,541,668 discloses a process for the preparation of atomoxetine hydrochloride involves reacting an alkoxide of N-methyl-3-phenyl-3-hydroxy propyl amine or an N-protected derivative thereof, with 2-fluorotoluene at temperature 110° C. for 20 hours in 1,3-dimethyl-2-imidazolidinone (DMI) or N-methyl-3-pyrolidinone (NMP) as solvents. Further the process persists to form (S)-(+)-mandelate salt with the help of seeding (R)-tomoxetine (S)-(+)-mandelic acid salt. Then (R)-tomoxetine (S)-(+)-mandelate salt is basified and extracted with methyl t-butyl ether. Water is removed by azeotropic distillation and hydrogen chloride is added to give atomoxetine hydrochloride.

The main disadvantages of the above process is to use the solvent like DMI is well known for its toxic effect in contact with skin and NMP has been identified as a reproductive toxicant, first by California office of environmental health hazard assessment (OEHHA) in 2001. This process involves disadvantages as long reaction time, tedious and more number of operations and large solvent volumes those are incompatible with large-scale industrial synthesis. Moreover, the patent does not disclose product yield and purity as well.

U.S. Pat. No. 7,507,861 discloses a process for the preparation of atomoxetine hydrochloride as described below: N-methyl-3-hydroxy-3-phenylpropylamine is taken in dimethyl sulphoxide and potassium hydroxide and heated to 110° C. Then the mixture is vacuum distilled to remove 130 gm solvent from 1100 gm. After this procedure 2-fluorotoluene is added to the reaction mass and heated as high as 145-147° C. Then water and toluene is added. After separation of organic phase the reaction proceed to prepare (R)-(−)-tomoxetine (S)-(+)-mandelate. The reaction involves (R)-(−)-tomoxetine (S)-(+)-mandelate in toluene and water (1:1) treating with 30% sodium hydroxide solution to convert (R)-(−)-tomoxetine (S)-(+)-mandelate into (R)-(−)-tomoxetine free base. The phase are separated and concentrated the organic layer to give (R)-(−)-tomoxetine free base oil. The obtained free base oil is dissolved into 9 volumes of ethyl acetate at low temperature about 12° C. followed by addition of gaseous hydrogen chloride to give atomoxetine hydrochloride.

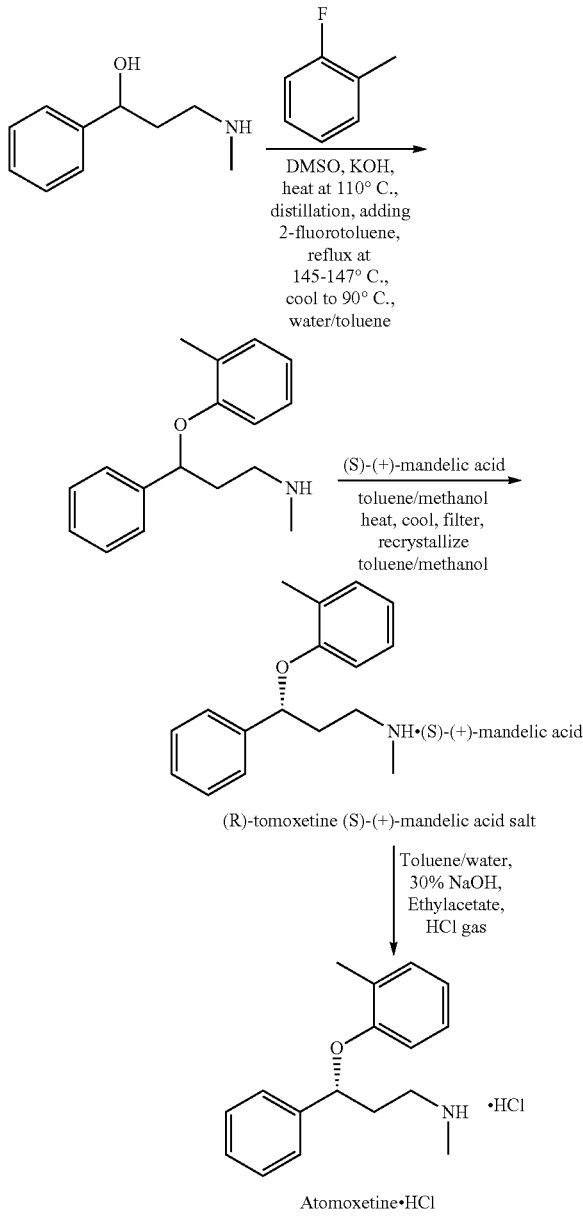

The main disadvantage of the process is distillation in first stage makes the process unattractive from the operation point of view. Use of gaseous hydrogen chloride is very much critical to handle at the plant level. Moreover, gaseous hydrogen chloride generates white fumes upon contacting with humidity which can be hazardous to the health when inhaled. As per the observation of scientist of the present invention that in the first stage of condensation, the continuous removal of water is necessary to complete the reaction otherwise reaction will remain incomplete and needed more efforts to remove impurities from the incomplete reaction.

WO 2006/037055 A1 discloses the (±)-atomoxetine oxalate having crystalline form II. As disclosed in the below scheme, the process for preparing oxalate salt of tomoxetine is very lengthy, cumbersome and several operations make the process industrially uneconomical as well as unviable. Moreover that the yield obtained is 55% after very lengthy process, which is not satisfactory from the industrial point of view. Again preparation of (S)-(+)-mandelate salt from the oxalate salt is also not attractive due the use of various solvents including petroleum ether. Use of autoclave and treatment of the material with two different alkalis is not understandable or unjustifiable from the chemistry point of view. Three time distillation at the condensation stage make the process very lengthy, cumbersome and unattractive from the plant point of view. Purification at condensation stage with acetone and petroleum ether leads the process to loss of yield. Further the conversion to atomoxetine hydrochloride gives around 73% yield. The process is depicted in below scheme.

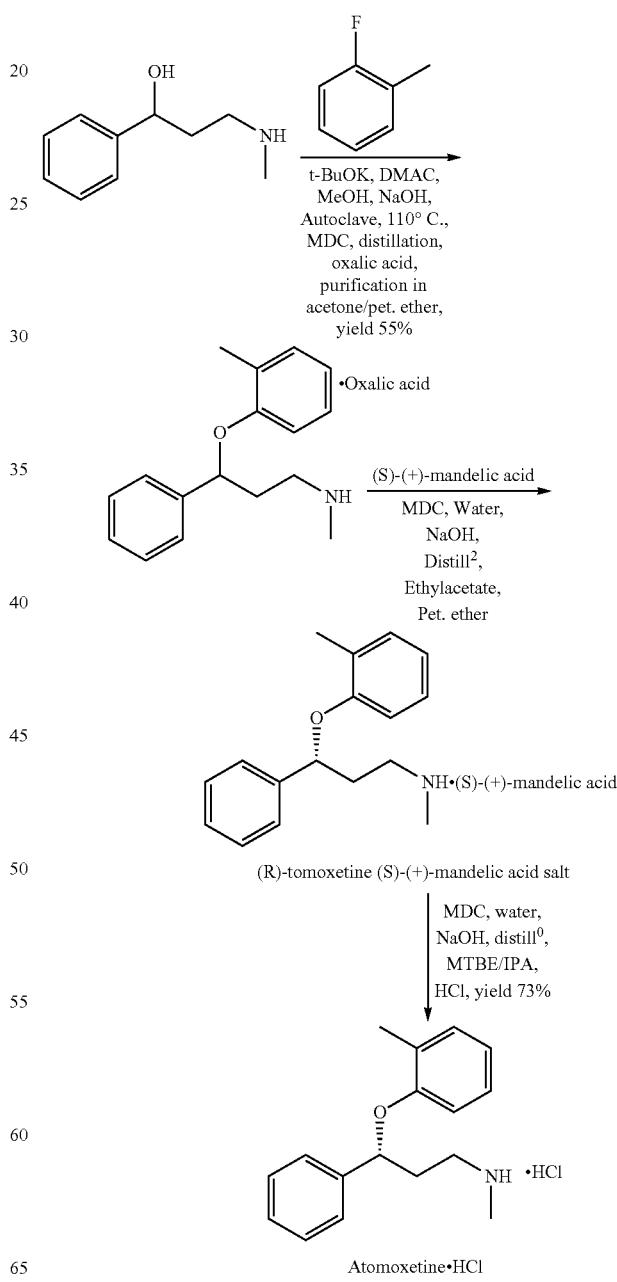

WO 2008/062473 A1 discloses the process for the preparation of atomoxetine hydrochloride starting from the condensation of o-cresol and N,N-dimethyl-3-chloro-3-phenyl-propylamine to form N,N-dimethyl-3-(o-methylphenoxy)-3-phenyl-propylamine followed by demethylation by treating with phenyl chloroformate in the presence of tri-ethylamine and subsequently reacted with oxalic acid to isolate oxalic acid salt of tomoxetine having crystalline form I converted to (±)-atomoxetine free base which is then reacted with (S)-(+)-mandelic acid to form (S)-(+)-mandelic acid salt of (R)-tomoxetine. The obtained salt is treated with alkali and converted to atomoxetine hydrochloride by treatment with IPA-HCl. The yield is as low as about 71%. The disclosed process is operationally very lengthy and tedious as depicted in the below process scheme. In condensation stage lots of operations are involved which make it very cumbersome. The process involves additional operation like demethylation which leads to loss of yield. Moreover this, use of industrial o-cresol at large scale is not a good option as commercial o-cresol contains contamination of p-cresol, phenol, 2,6-xylenol which can be carried forward up to the last stage of API; hence exhaustive purification is required to remove the impurities.

Yet another objective of the invention is to provide an efficient, improved and industrially advantageous process for preparation of atomoxetine hydrochloride which is conveniently applicable to industrial scale.

Yet more objective of the present invention is to provide a process the preparation of atomoxetine hydrochloride having high purity and yield as well.

Yet one more objective of the present invention is to provide a process for the preparation of tomoxetine in-situ via continuous water removal during condensation reaction.

Yet additional object of the present invention is to provide pure atomoxetine hydrochloride having HPLC purity more than 99.5% and chiral HPLC ratio R/S>99.9/0.1.

SUMMARY OF THE INVENTION

Accordingly, the present invention provides an improved process for the preparation of atomoxetine hydrochloride of formula I.

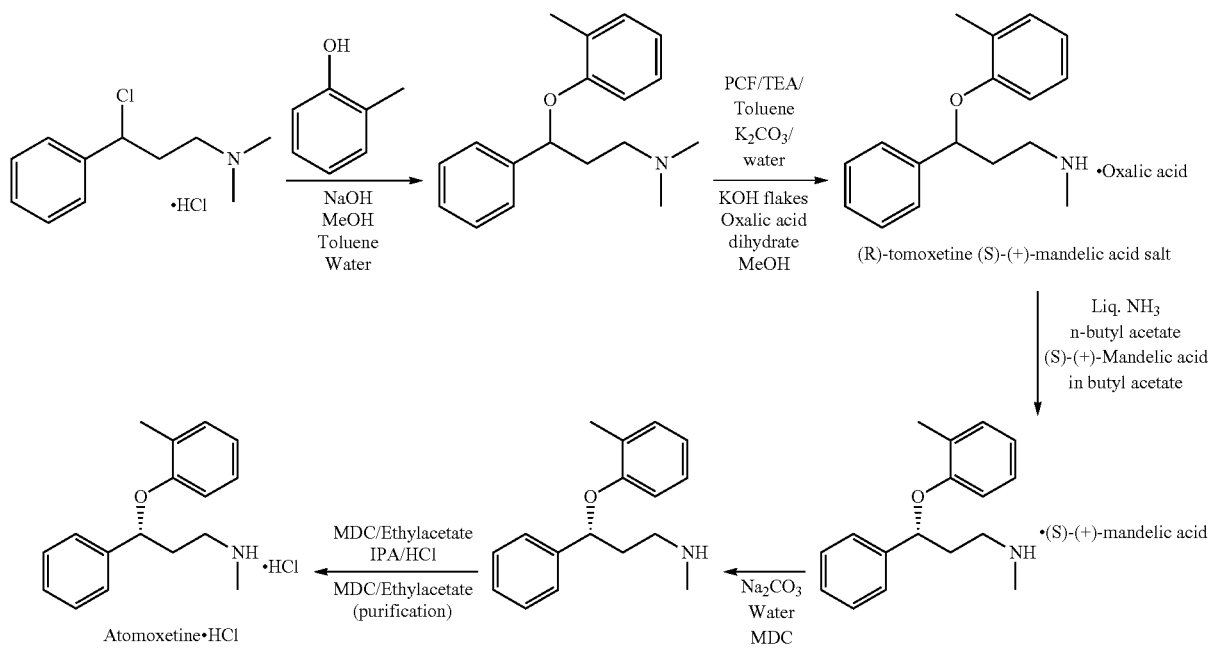

WO 2006/020348 discloses the crystalline polymorphic forms, Form A, Form B and Form C of Atomoxetine hydrochloride. WO 2006/020348 further discloses that the repetition of the processes disclosed in EP 052,492 and U.S. Pat. No. 6,541,668 yielded a crystalline form of Atomoxetine hydrochloride denominated as Form A.

Thus, present invention fulfills the need of the art and provides an improved and industrially applicable process for preparation of atomoxetine hydrochloride, which provides atomoxetine hydrochloride in high purity and good yield.

OBJECTIVE OF THE INVENTION

The principal objective of the present invention is to provide a process for preparation of atomoxetine hydrochloride to overcome or ameliorate one of the disadvantages of the prior art processes

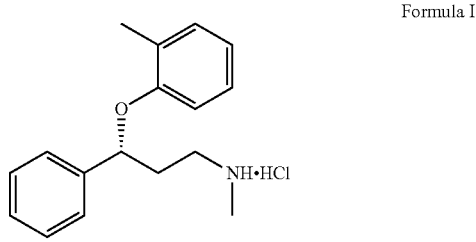

Formula I which proves to be efficient and industrially viable. The process comprises the steps of:
a). condensing the compound of formula II with 2-fluorotoluene in the presence of inorganic base in high boiling point polar aprotic solvent;

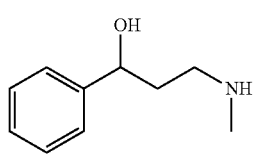

Formula II b). extracting the reaction mixture in hydrocarbon solvent;
c). treating with oxalic acid solution in isopropyl alcohol;
d). isolating oxalic acid salt of tomoxetine of formula III;

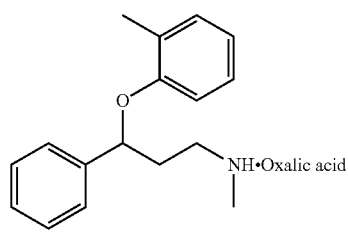

Formula III e). basifying compound of formula III in hydrocarbon solvent;
f). treating obtained free base with (S)-(+)-mandelic acid in ester solvent;
g). isolating (S)-(+)-mandelic acid salt of (R)-tomoxetine of formula IV;

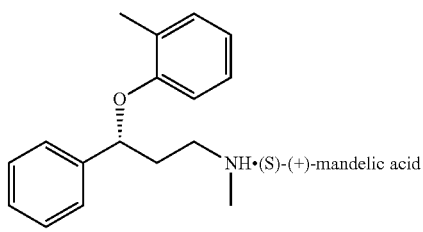

Formula IV h). basifying (S)-(+)-mandelic acid salt of (R)-tomoxetine formula IV in mixture of water and hydrocarbon solvent;
i). separating the layers and distilling the hydrocarbon solvent;
j). adding the mixture of ether and nitrile solvent in residue;
k). treating with alcoholic hydrochloric acid to form atomoxetine hydrochloride of formula I; and
l). purifying atomoxetine hydrochloride of formula I in suitable solvent.

Accordingly, the present invention provides a process for the preparation of compound of formula III, process comprises the step of:

a) condensing the compound of formula II with 2-fluorotoluene in the presence of inorganic base in high boiling point polar aprotic solvent, b) extracting the reaction mixture in hydrocarbon solvent;

c) treating with oxalic acid dihydrate solution in isopropyl alcohol;

d) isolating oxalic acid salt of tomoxetine formula III;

Accordingly, the present invention provides a process for the preparation of tomoxetine in-situ comprises continuous water removal during condensation of 2-fluorotoluene and compound of formula II.

Accordingly, the present invention provides a process for preparing pure atomoxetine hydrochloride having HPLC purity more than 99.5% and chiral HPLC ratio R/S>99.9/0.1 obtained from (S)-(+)-mandelic acid salt of (R)-tomoxetine formula IV having HPLC purity 97±1% and chiral HPLC ratio R/S::90/10±3.

Accordingly, the present invention provides an improved process for the preparation of pharmacopoeial grade atomoxetine hydrochloride as depicted in below scheme:

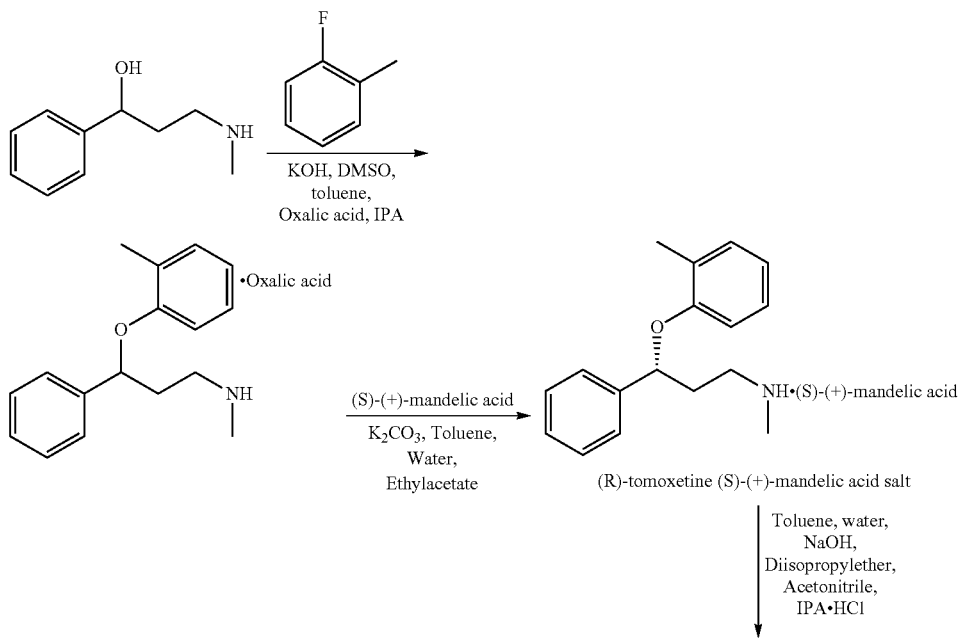

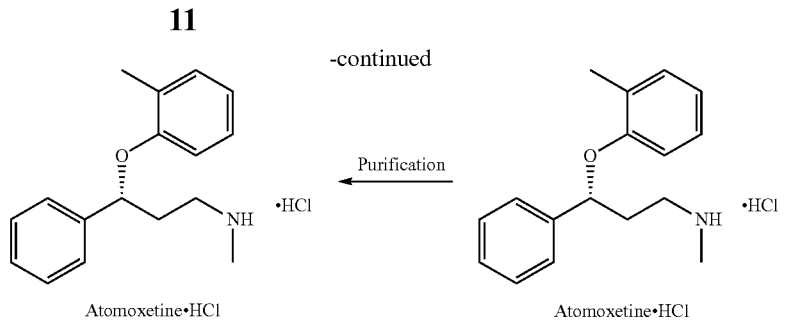

Atomoxetine·HCl ← Purification ← Atomoxetine·HCl

DETAILED DESCRIPTION OF THE INVENTION

All ranges recited herein include the endpoints, including those that recite a range "between" two values. Terms such as "about", "generally" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

As used herein, the term "ambient temperature" describing common indoor temperatures usually falls in the range of 25 to 35° C.

The present invention provides an improved and efficient process for the preparation of atomoxetine hydrochloride of formula I.

According to the embodiment of the invention provides an industrially viable process for preparation of atomoxetine hydrochloride starting from compound of formula II.

Stage 1:

The compound of formula II is reacted with 2-fluorotoluene in the presence of inorganic base in high boiling point polar aprotic solvent to form tomoxetine in-situ followed by reaction with oxalic acid to give oxalic acid salt of tomoxetine of formula III. Generally the reaction involves treatment of compound of formula II with 2-fluorotoluene in the presence of inorganic base. Suitable inorganic base include alkali or alkaline metal hydroxides, carbonates, bicarbonates, alkoxides; wherein inorganic base is preferably sodium hydroxide, potassium hydroxide, lithium hydroxide, sodium carbonate, potassium carbonate, lithium carbonate, sodium bicarbonate, potassium bicarbonate, lithium bicarbonate; wherein inorganic base is more preferably potassium hydroxide. Suitable high boiling point polar aprotic solvent includes dimethyl sulphoxide, dimethylformamide and the like in any suitable proportion in the mixture with toluene. The reaction mixture is heated at 40-150° C. for 1 to 24 hours, preferably for 8-9 hours at temperature about 125-130° C. for the purpose to remove the water azeotropically. The reaction mixture is cooled to ambient temperature and water is added. The layers are separated. The organic layer is treated with oxalic acid in isopropyl alcohol. The reaction mixture is stirred for sufficient time to form the oxalic acid salt of tomoxetine.

Particularly, compound of formula II is reacted with 2-fluoro toluene in the presence of potassium hydroxide in dimethyl sulphoxide or dimethyl formamide and toluene. The reaction mixture is heated at temperature 126-128° C. for 8-9 hours to form tomoxetine in-situ. During condensation, water is formed in the reaction mixture and it is removed azeotropically in continuous manner. The reaction mixture is then cooled to ambient temperature followed by addition of water and stirred for about 1 hour followed by layer separation. The organic layer is treated with oxalic acid solution in isopropyl alcohol and stirred for about 1 hour. The mass is filtered at ambient temperature and washed with toluene and isopropyl alcohol as well. The formed oxalic acid salt of tomoxetine of formula III is dried in vacuuo having HPLC purity more than 98.5%.

The main advantage of this particular step is to make the process plant friendly and industrially viable in terms of yield, quality and operations. In addition, scientists of the present invention observe that continuous removal of water during condensation, the reaction complies very fast and resulted in very good yield. The reported prior art processes as described in the background of the invention having drawbacks such as long reaction process, tedious workup procedure, distillation of solvent at high temperature, use of large volume solvents, purification in solvents like petroleum ether. Other advantage of the present invention is to prepare purer oxalate salt of tomoxetine by such a way which leads to removal of major impurities as well as starting material. The present invention provides very good quality oxalate salt of tomoxetine that gives desired quality tomoxetine free base.

Moreover that the prior art processes involve demethylation by phenyl chloroformate and subsequent conversion to oxalic acid salt of tomoxetine; which involves more unit operations and resulted in around 52% yield. Hence the prior art processes are not economically viable. The present invention is ameliorating the major involved drawbacks of the prior art processes.

Stage 2:

The compound of formula III is reacted with base in hydrocarbon solvent to form tomoxetine free base in-situ followed by treating with (S)-(+)-mandelic acid in ester solvent. Generally the reaction involves basifying compound of formula III with base. Suitable base include inorganic base, wherein inorganic base includes alkali or alkaline metal hydroxides, carbonates, bicarbonates, alkoxides; wherein base is preferably sodium hydroxide, potassium hydroxide, lithium hydroxide, sodium carbonate, potassium carbonate, lithium carbonate, sodium bicarbonate, potassium bicarbonate, lithium bicarbonate and the like; wherein base is more preferably potassium carbonate. Suitable hydrocarbon solvent includes toluene or xylene in any suitable proportion or mixtures thereof; wherein hydrocarbon solvent used with mixture of water. The reaction mixture is stirred for sufficient time at ambient temperature and layers are separated. Solvent is removed under vacuum and obtained residue dissolved in ester solvent followed by treating with (S)-(+)-mandelic acid. Suitable ester solvent includes ethyl acetate, isopropyl acetate or methyl acetate in any suitable proportion or mixtures thereof. The reaction mixture is heated and stirred at temperature 40-70° C. for 1-4 hours, preferably at 45-50° C. for 2 hours followed by cooling at temperature −5-10° C., preferably at 0-5° C. to give compound of formula IV.

Particularly, compound of formula III is treated with solution of potassium carbonate in mixture of water and toluene. The reaction mixture is stirred at ambient temperature for 30 minutes and layers are separated. The organic layer is distilled out under vacuum at temperature about 75-80° C. The obtained residue is cooled to ambient temperature to get tomoxetine free base. The free base is treated with (S)-(+)-mandelic acid in ethyl acetate. The reaction mixture is heated and stirred at temperature 45-50° C. for 2 hours followed by cooling at temperature 0-5° C. to give compound of formula IV. The reaction mixture is then filtered and washed with chilled ethyl acetate. The isolated formula IV dried at 50-55° C. having HPLC purity more than 99.5%, enantiomeric ratio R/S>90/10 by chiral HPLC.

The advantages of this particular stage are to avoid longer reaction time and tedious workup as well. The compound of formula IV obtained by the present invention have purity more than 90%, preferably more than 95%, more preferably greater than 99%.

Stage 3:

The reaction involves compound of formula IV is reacted with inorganic base in mixture of hydrocarbon solvent and water in any suitable proportion or mixtures thereof. Generally the reaction involves basifying compound of formula IV with inorganic base. Suitable inorganic base include alkali or alkaline metal hydroxides, carbonates, bicarbonates, alkoxides; wherein base is preferably sodium hydroxide, potassium hydroxide, lithium hydroxide, sodium carbonate, potassium carbonate, lithium carbonate, sodium bicarbonate, potassium bicarbonate, lithium bicarbonate and the like; wherein base is more preferably sodium hydroxide. Suitable hydrocarbon solvent includes toluene or xylene in any suitable proportion or mixtures thereof; wherein hydrocarbon solvent used with mixture of water. The reaction mixture is stirred for sufficient time at ambient temperature and layers are separated. The organic layer is distilled out under vacuum to obtain atomoxetine free base residue. In to the residue, mixture of ether and nitrile solvent is added. Suitable ether solvent includes diethyl ether or diisopropyl ether in any suitable proportion or mixtures thereof and suitable nitrile solvent includes acetonitrile, or propionitrile in any suitable proportion or mixtures thereof. The reaction mixture is added IPA-HCl and stirred for a while. The reaction mixture is then cooled to 0-10° C. and maintained for 1-5 hours, preferably 0-5° C. and maintained for about 1 hour to give compound of formula I.

Particularly, compound of formula IV is treated with 20% sodium hydroxide solution in mixture of toluene and water. The reaction mixture is stirred for while and layers are separated. The organic layer is distilled out under vacuum at temperature 75-80° C. followed by addition of mixture of diisopropyl ether and acetonitrile into the residue. Further IPA-HCl is added into the reaction mixture and stirred for a while. The reaction mixture is cooled to 0-5° C. and maintained for 1 hour followed by filtration of the mass. The obtained compound of formula I is washed with diisopropyl ether and dried to give atomoxetine hydrochloride of formula I having HPLC purity more than 99.5%.

The main advantage of this stage is to enhance the yield of atomoxetine hydrochloride. As reported yields in the prior art processes viz WO2006/037055 and WO2008/062473 are around 70-73% whereas present invention resulted in around 83% yield. It is a great advantage of the invention from the economic and industrial point of view. As compared to prior art processes, 10% higher yield makes the process cost-effective and industrially viable.

Stage 4:

Generally, The purification of atomoxetine hydrochloride of formula I involves use of solvents such as hydrocarbon, alcohol and nitrile; wherein alcohols include methanol, ethanol, n-propanol or isopropanol, hydrocarbons include toluene or xylene, nitriles include acetonitrile or propionitrile and/or mixtures thereof. The reaction mixture is heated to 50-100° C. and stirred for while. The reaction mixture is then cooled to ambient temperature to give pure atomoxetine hydrochloride of formula I. To achieve very high quality of atomoxetine hydrochloride formula I (i.e HPLC purity >99.5%), second time purification can also be given with the same solvent by repeating the same process.

Particularly, atomoxetine hydrochloride is dissolved in a solvent such as nitrile, hydrocarbon and alcohol or mixtures thereof. The reaction mixture is then stirred for 5-10 minutes and gradually cooled to ambient temperature. Further the mass stirred for 1 hour, filtered, washed with acetonitrile and dried under vacuum to give atomoxetine hydrochloride having HPLC purity more than 99.5%.

The scientists of the present invention designed the process in a manner in which atomoxetine hydrochloride obtained desired quality without purifying (S)-(+)-mandelic acid salt of (R)-tomoxetine formula IV (HPLC purity >98.0, chiral purity ratio R/S>90/10). Hence present invention ameliorating drawbacks of the prior art process patents as described in the background of the invention. The chiral purity ratio i.e desired enantiomeric purity is achieved by using a specific combination of solvents in stage 3 of the present invention, such as nitrile, ether and alcohol which affords desired chiral purity as well as HPLC purity. Starting from (S)-(+)-mandelic acid salt of (R)-tomoxetine having chiral purity ratio R/S>90/10 where as atomoxetine hydrochloride having chiral purity ratio at least R/S>99.85/0.15 which is pharmacopoeially acceptable. The trend of purity as well as chiral purity in the present invention at each stage shows that the purity is increasing without compromising with yield. Moreover it is observed that the commercial 2-fluoro toluene is contaminated with 3-fluoro toluene and 4-fluoro toluene which is converted in and corresponding substituted atomoxetine hydrochloride i.e (R)-(−)-N-Methyl-3-phenyl-3-(m-tolyloxy)propan-1-amine hydrochloride and (R)-(−)-N-Methyl-3-phenyl-3-(p-tolyloxy)propan-1-amine hydrochloride. The above generated isomeric impurities are also reduced in purification step. The process of the present invention is economically viable due to good yield, plant friendly due to less operation involved and meeting the regulatory requirements of quality.

The invention is further defined by reference to the following examples describing in detail by the preparation of the compounds of the invention. It will be apparent to those skilled in the art that many modifications, both to materials and methods, may be practiced without departing from the scope of the invention.

EXAMPLES

Stage 1: Preparation of Oxalic Acid Salt of Tomoxetine (Formula III)

To a stirred solution of potassium hydroxide (254.6 gm) in toluene (1000 ml), dimethyl sulphoxide (1750 ml) and 3-methylamino-1-phenyl-1-propanol (250 gm) were added at ambient temperature followed by addition of 2-fluoro toluene (499.75 gm) into the reaction mass. The reaction mass was heated up to the temperature at 126-128° C. for 8-9 hours with azeotropic distillation to remove water, cooled to ambient temperature and water (1750 ml) was added into it. The reaction mass was stirred and the layers were separated. The aqueous layer extracted with toluene and washed with water. The organic layers were combined. To a stirred organic layer, oxalic acid solution {oxalic acid.2H$_2$O (195 gm)+isopropylalcohol (750 ml)} was added and further stirred for 1 hour. The reaction mass was then filtered at ambient temperature and washed with toluene (2×250 ml) followed by washing with isopropyl alcohol (2×250 ml). The product was suck dried and further dried in vacuuo at 65-70° C. for 2-3 hours to give 425-430 gm of title compound.

HPLC purity: >99%
Isomeric impurity:
N-Methyl-3-phenyl-3-(m-tolyloxy)propan-1-amine oxalate 0.5-1.0%,
N-Methyl-3-phenyl-3-(p-tolyloxy)propan-1-amine oxalate 1.0-2.0%.

Stage 2: Preparation of (S)-(+)-Mandelic Acid Salt of (R)-Tomoxetine (Formula IV)

In to a solution of water (1237.5 ml), potassium carbonate (247.2 gm) and toluene (1237.5 ml), stage 1 (412.5 gm) was added lot wise. The reaction mass was stirred for 30 minutes and the layers were separated. The aqueous layer was extracted with toluene (412.5 ml). The organic layers were combined and washed with water (412.5 ml). The organic layer was distilled out under vacuum at temperature 75-80° C. and degassed the residue. Then residue was cooled to ambient temperature. Into the residue of tomoxetine free base, ethyl acetate (1206 ml) was added followed by addition of S-(+)-mandelic acid (96.48 gm). The reaction mass was heated at temperature 45-50° C. for 2 hours and cooled to temperature 0-5° C. The reaction mass was filtered and washed with chilled ethyl acetate. The product was suck dried and further dried in tray drier at 50-55° C. to give 171.5 gm of title compound.

HPLC purity: >98%
Chiral HPLC ratio: R/S>90/10
Isomeric impurity:
(R)-(−)-N-Methyl-3-phenyl-3-(m-tolyloxy)propan-1-amine (S)-(+)-mandelate 0.4-0.6%
(R)-(−)-N-Methyl-3-phenyl-3-(p-tolyloxy)propan-1-amine (S)-(+)-mandelate 1.5-1.8%

Stage 3: Preparation of Atomoxetine Hydrochloride (Formula I)

Into the reaction assembly water (990 ml), toluene (990 ml) and stage 2 were added at ambient temperature. The pH of the reaction mass was adjusted using 20% sodium hydroxide (48.5 gm dissolved in 194.6 gm process water). The reaction mass was then stirred and layers were separated. The aqueous layer was extracted with toluene. The organic layers were combined. The organic layer was washed with water (165 ml×2). The organic layer was distilled out under vacuum at temperature 75-80° C. Acetonitrile (99 ml) and diisopropyl ether (297 ml) was added into the obtained residue followed by addition of IPA-HCl (165 ml). The reaction mass was stirred, cooled to 0-5° C. and maintained for 1 hour followed by filtration of the mass. The obtained material washed with diisopropyl ether (165 ml). The product was suck dried and further dried in tray drier at 55-60° C. to give 99 gm of title compound.

HPLC purity: >98.5%
Chiral HPLC ratio: R/S>97/3
Isomeric impurity:
(R)-(−)-N-Methyl-3-phenyl-3-(m-tolyloxy)propan-1-amine hydrochloride 0.1-0.3%
(R)-(−)-N-Methyl-3-phenyl-3-(p-tolyloxy)propan-1-amine hydrochloride 0.5-0.8%.

Stage 4: Purification of Atomoxetine Hydrochloride (Formula I)

Into acetonitrile (450 ml), atomoxetine hydrochloride stage 3 (90 gm) was added. The reaction mass was heated at temperature 78-84° C. and stirred for 5-10 minutes. The reaction mass was then cooled gradually at ambient temperature and stirred for 1 hour. The reaction mass was filtered and the cake was washed with acetonitrile (90 ml). The product was dried under vacuum to give 81 gm of title compound.

HPLC purity: >99.5%
Chiral HPLC ratio: R/S>99.97/0.03
Isomeric impurity:
(R)-(−)-N-Methyl-3-phenyl-3-(m-tolyloxy)propan-1-amine hydrochloride <0.1%
(R)-(−)-N-Methyl-3-phenyl-3-(p-tolyloxy)propan-1-amine hydrochloride <0.1%.

We claim:
1. A process for preparing atomoxetine hydrochloride comprising the steps of:
   a). condensing the compound of formula II with 2-fluorotoluene in the presence of inorganic base in mixture of hydrocarbon and polar aprotic solvent with continuous water removal, wherein the water is formed during the condensation;

Formula II

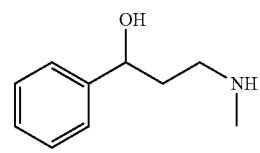

b). extracting the reaction mixture in an appropriate solvent, wherein the appropriate solvent is a hydrocarbon solvent;
   c). treating with oxalic acid solution in isopropyl alcohol;
   d). isolating oxalic acid salt of tomoxetine of formula III;

Formula III e). basifying compound of formula III in hydrocarbon solvent;

f). treating obtained mass without isolating free base with (S)-(+)-mandelic acid in ester solvent;

g). isolating (S)-(+)-mandelic acid salt of (R)-tomoxetine of formula IV;

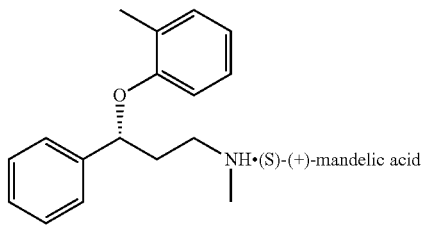

Formula IV h). basifying (S)-(+)-mandelic acid salt of (R)-tomoxetine of formula IV in mixture of water and hydrocarbon solvent;

i). separating the layers and distilling the hydrocarbon solvent;

j). adding the mixture of ether and nitrile solvents in residue;

k). treating with alcoholic hydrochloric acid to form atomoxetine hydrochloride of formula I; and l). purifying atomoxetine hydrochloride of formula I in suitable solvent.

2. The process according to claim 1, wherein in step a), polar aprotic solvent is selected from dimethyl sulphoxide or dimethylformamide or mixtures thereof;

in step a), e) or h), inorganic base is selected from sodium hydroxide, potassium hydroxide, lithium hydroxide, sodium carbonate, potassium carbonate, lithium carbonate, sodium bicarbonate, potassium bicarbonate or lithium bicarbonate;

in step a), b), e), h), or i), hydrocarbon solvent is selected from toluene or xylene or mixtures thereof;

in step f), ester solvent is selected from ethyl acetate, isopropyl acetate or methyl acetate or mixtures thereof;

in step j), ether solvent is selected from diethyl ether or diisopropyl ether or mixtures thereof and nitrile solvent is selected from acetonitrile or propionitrile or mixtures thereof; and in step l), suitable solvent is selected from alcohols include methanol, ethanol, n-propanol or isopropanol, hydrocarbons include toluene or xylene, nitriles include acetonitrile or propionitrile and/or mixtures thereof.

3. The process according to claim 1, wherein, pure atomoxetine hydrochloride having HPLC purity more than 99.5% and chiral HPLC ratio R/S>99.9/0.1 obtained from (S)-(+)-mandelic acid salt of (R)-tomoxetine formula IV having HPLC purity 97±1% and chiral HPLC ratio R/S:: 90/10±3.

4. The process according to claim 3, wherein (S)-(+)-mandelic acid salt of (R)-tomoxetine formula IV converted to atomoxetine free base residue by treating with base.

5. The process according to claim 4, wherein atomoxetine free base residue is treated with IPA-HCl in solvent combination of ether and nitrile to form atomoxetine hydrochloride.

6. The process according to claim 5, wherein atomoxetine hydrochloride optionally be purified with suitable solvent.

7. A process for the preparation of 3-Aryloxy-3-phenyl-propylamine and salt thereof of formula III, wherein said salt is an oxalate salt, the process comprising the steps of:

a). condensing the compound of formula II with 2-fluorotoluene in the presence of inorganic base in mixture of hydrocarbon and polar aprotic solvent with continuous water removal, wherein the water is formed during the condensation;

b). extracting the reaction mixture in hydrocarbon solvent;

c). treating with oxalic acid dihydrate solution in isopropyl alcohol; and isolating oxalic acid salt of tomoxetine of formula III.

8. The process according to claim 7, wherein in step a), polar aprotic solvent is selected from dimethyl sulphoxide or dimethylformamide or mixtures thereof in step a), inorganic base is selected from sodium hydroxide, potassium hydroxide, lithium hydroxide, sodium carbonate, potassium carbonate, lithium carbonate, sodium bicarbonate, potassium bicarbonate or lithium bicarbonate in step a) or b), hydrocarbon solvent is selected from toluene or xylene or mixtures thereof.

9. The process according to claim 7, comprises continuous water removal during condensation of 2-fluorotoluene and compound of formula II.

10. The process according to claim 9, wherein water is removed azeotropically from the reaction mixture.

* * * * *